(12) United States Patent
Bausch et al.

(10) Patent No.: US 8,420,700 B1
(45) Date of Patent: Apr. 16, 2013

(54) TAMPER RESISTANT LIPID-BASED ORAL DOSAGE FORM FOR SYMPATHOMIMETIC AMINES

(76) Inventors: James M. Bausch, Wildwood, MO (US); Alvin Kershman, Chesterfield, MO (US); Jeff Shear, Glenview, IL (US); Linda L Lewis, Pacific, MO (US)

( * ) Notice: Subject to any disclaimer, the term of this patent is extended or adjusted under 35 U.S.C. 154(b) by 0 days.

(21) Appl. No.: 13/547,365

(22) Filed: Jul. 12, 2012

Related U.S. Application Data

(63) Continuation-in-part of application No. 12/156,775, filed on Jun. 4, 2008, now Pat. No. 8,273,798.

(51) Int. Cl.
*A61K 9/00* (2006.01)
*A61K 47/00* (2006.01)

(52) U.S. Cl.
USPC .......................................... 514/785; 424/498

(58) Field of Classification Search .................. None
See application file for complete search history.

(56) References Cited

U.S. PATENT DOCUMENTS

| | | | |
|---|---|---|---|
| 6,309,668 B1* | 10/2001 | Bastin et al. | 424/472 |
| 6,419,954 B1* | 7/2002 | Chu et al. | 424/465 |
| 6,709,669 B1* | 3/2004 | Murray et al. | 424/434 |
| 2003/0049315 A1* | 3/2003 | Daggy et al. | 424/465 |
| 2007/0026074 A1* | 2/2007 | Martin et al. | 424/488 |

FOREIGN PATENT DOCUMENTS

WO   WO 03013479 A1 *   2/2003

OTHER PUBLICATIONS

Sriamornsak P, Sungthongjeen S. Modification of Theophylline Release With Alginate Gel Formed in Hard Capsules. AAPS PharmSciTech. 2007; 8(3): Article 51 E1-E8.*

* cited by examiner

*Primary Examiner* — Robert A Wax
*Assistant Examiner* — Olga V Tcherkasskaya
(74) *Attorney, Agent, or Firm* — CreatiVenture Law, LLC; Linda L. Lewis

(57) ABSTRACT

A tamper resistant drug delivery system made of at least one lipid, at least one gelling agent and at least one sympathomimetic amine, such as for example pseudoephedrine, wherein the system gels in the presence of water or a solution containing water and ethanol, wherein the sympathomimetic amine releases into the digestive system when ingested, and wherein the weight ratio of gelling agent to lipid is less than 1:1.4.

20 Claims, No Drawings

TAMPER RESISTANT LIPID-BASED ORAL DOSAGE FORM FOR SYMPATHOMIMETIC AMINES

RELATED APPLICATIONS

This applications claims the benefit of provisional application 60/933,031 filed Jun. 4, 2007, now application Ser. No. 12/156,775, filed Jun. 4, 2008.

FIELD OF THE INVENTION

The field of the invention is oral dosage forms of sympathomimetic amines. More specifically, the field is lipid-based oral dosage combined with a gelling agent for sympathomimetic amines that is tamper-resistant in that the sympathomimetic amine is not easily converted to methamphetamine. While being abuse-resistant, the dosage form also effectively releases into the digestive system when ingested.

BACKGROUND OF THE INVENTION

The acid salts of sympathomimetic amines, for example, pseudoephedrine hydrochloride, are widely used active agents in over-the-counter (OTC) pharmaceuticals. As their name suggests, this class of compounds produces pharmacological effects which mimic the activation of the sympathetic nervous system. For example, the acid salt of the sympathomimetic amine, pseudoephedrine hydrochloride is a commonly used active ingredient in OTC decongestant products. It acts by causing adrenergic nerve endings to release norepinephrine, thereby stimulating alpha and beta norepinephrine receptors, particularly of the upper respiratory tract. This, in turn, results in vasoconstriction and shrinkage of swollen tissues in the sinuses and nasal passages. Its wide usage in numerous OTC products makes it readily available and easily accessible to the general public. When used in a recommended manner for approved indications, OTC pseudoephedrine hydrochloride pharmaceuticals are safe and effective. However, a problem arises when pseudoephedrine hydrochloride-containing OTC pharmaceuticals are used in an unconventional manner. Specifically, this active ingredient from OTC products is also a convenient starting material in the production of the pharmacologically active agent methamphetamine. The following references are directed to tamper resistant pseudoephedrine formulations.

U.S. Pat. No. 6,852,891 discloses a method of inhibiting or preventing the use of anhydrous ammonia as a solvent in a dissolving metal reduction process by adding to anhydrous ammonia a chemical reagent which is capable of scavenging solvated electrons generated when an alkali or alkaline earth metal is dissolved in the anhydrous ammonia containing the chemical reagent to make meth.

U.S. Pat. No. 6,359,011 and related application 2005/0256194 disclose denaturants for sympathomimetic amine salts. The denaturants include combination inhibitors, such as amino polymers, neutralized or as its salt, including salts of transition metals; reaction inhibitors such as water insoluble polyhydroxyl compounds, water soluble polyhydroxyl compounds and solvent soluble esters; and separation inhibitors such as gelling agents.

U.S. Pat. No. 6,136,864 discloses denaturants for sympathomimetic amine salts. In addition to the denaturants listed in the previous paragraph, this patent includes odor producing denaturants and encapsulated non-polar solvent soluble soap precursors and surfactants. The soap precursors include fatty acids and fatty acid esters. These products are encapsulated in a water-insoluble capsule so that they will not be released or extracted during non-polar solvent extraction, but will release in water extraction. They are viewed as being able to physically interfere with the pseudoephedrine extraction and purification, because of their effectiveness as a surfactant.

U.S. Pat. No. 6,197,314 discloses tablets containing gelling agents, with or without fats, and surfactants to impede the extraction of pseudoephedrine. In every solid dosage form using fats, the amount of fat is from about one half to one third the amount of the drug active, and much less than the claimed 20 to 50 wt. % of the present delivery system.

Tamper-resistant delivery systems using gelling agents in a drug delivery form are known in the art. When the dosage is dissolved in a small amount of water, instead of a solution, a viscous gel that cannot be injected may be formed. For combination drug systems, the gel prevents the acetaminophen from being removed by cold water extraction, because the gel retains the drugs together when extraction is attempted. U.S. Pat. Nos. 3,980,766 and 4,070,494 and U.S. patent application publications 2003/0068471, 2003/0068375, and 2007/0014732 disclose the use of gelling agents to create tamper-resistant drug delivery forms. However, often, if the amount of gelling agent is present in a sufficient amount to prevent extraction, it slows or defeats release upon ingestion.

The present application discloses that gelling agents can hinder the release of the sympathomimetic amine upon ingestion, thereby defeating the usefulness of the medication. However, the combination of an effective amount of gelling agent with a lipid can provide both the desired rapid gelling in the presence of an aqueous solvent and the desired release of the drug in the digestive system.

More importantly, the present application is directed to an orally ingested delivery system for sympathomimetic amines, particularly the acid salt of pseudoephedrine, which hinders the conversion of the pseudoephedrine acid salt to methamphetamine.

SUMMARY OF THE INVENTION

The present invention is a lipid-based oral dosage form of the acid salts of sympathomimetic amines that is tamper-resistant, in that the dosage cannot be easily extracted with either an aqueous solvent or an organic solvent to convert the sympathomimetic amine to methamphetamine. The lipid-based oral dosage contains sufficient lipid, i.e., from about 20 to 50 wt. % of the dosage form, to provide malleability at room temperature, i.e., 20 to 25° C. The lipid-based dosage form contains a gelling agent that gels in the presence of water or a solution containing water and ethanol. The gelling agent: lipid weight ratio is less than about 1:1.4, because at higher ratios, the dosage form does not effectively release the drug when ingested.

DETAILED DESCRIPTION OF THE INVENTION

The following description of the preferred embodiment(s) is merely exemplary in nature and is in no way intended to limit the invention, its application or uses.

The drug active includes sympathomimetic amines which cause vasoconstriction in the vascular bed of the nasal mucosa resulting in a shrinking of the engorged mucous membranes. Sympathomimetic amines are highly effective as nasal decongestants. Unless otherwise stated, as used herein the term "sympathomimetic amine" can be used interchangeably with and may refer to a corresponding pharmaceutically acceptable acid salt form of the amine. The amine and its acid salt form may have asymmetric centers and occur as racemates, racemic mixtures, individual diastereomers, or enantiomers, with all isomeric forms being included in the present invention. Those sympathomimetic amines widely available as OTC nasal decongestants are particularly contemplated for use in the instant invention; specific preferred examples include: pseudoephedrine hydrochloride, pseudoephedrine sulfate, ephedrine hydrochloride and phenylpropanolamine hydrochloride. The sympathomimetic amine phenylephrine hydrochloride is also contemplated in the instant invention.

While the descriptions and examples of the formulations may use a specific sympathomimetic amine such as pseudoephedrine hydrochloride, it is understood that the formulations are applicable to any composition comprising sympathomimetic amines and their corresponding acid salt forms. Combinations of the sympathomimetic amines with other drugs are within the scope of the present invention. stimulants such as gamma-hydroxybutyrate, dextroamphetamine, methylphenidate, sibutramine, methylenedioxymethamphetamine, pharmaceutically acceptable salts thereof, and the like; and other agents such as marinol, meprobamate, carisoprodol, and their precursors, such as pseudoephedrine, and pharmaceutically acceptable salts thereof and the like.

Various gelling agents can be employed including, for example and without limitation, sugars or sugar derived alcohols, such as mannitol, sorbitol, and the like, starch and starch derivatives, cellulose derivatives, such as microcrystalline cellulose, sodium caboxymethyl cellulose, methylcellulose, ethyl cellulose, hydroxyethyl cellulose, hydroxypropyl cellulose, and hydroxypropyl methylcellulose, attapulgites, bentonites, dextrins, alginates, carrageenan, gum tragacanth, gum acacia, guar gum, xanthan gum, pectin, gelatin, kaolin, lecithin, magnesium aluminum silicate, the carbomers and carbopols, polyvinylpyrrolidone, polyethylene glycol, polyethylene oxide, polyvinyl alcohol, silicon dioxide, surfactants, mixed surfactant/wetting agent systems, emulsifiers, other polymeric materials, and mixtures thereof, etc. The pectin or pectic substances useful for this invention include not only purified or isolated pectates but also crude natural pectin sources, such as apple, citrus or sugar beet residues which have been subjected, when necessary, to esterification or de-esterification, e.g., by alkali or enzymes. Preferably, the pectins used in this invention are derived from citrus fruits such as lime, lemon, grapefruit, and orange.

A preferred gelling agent is one that gels rapidly in the presence of water, e.g., thickens in about 10 seconds or less. Preferred gelling agents are hyaluronic acid or its salt, carboxymethyl cellulose (CMC), guar gum, and a combination of guar gum and xantham gum. A commercial source of a combination of guar gum and xantham gum is TIC Pretested® Action Gum 1144 Powder, sold by TIC GUMS, Inc. This gelling agent gels within 10 seconds of contact with water and is suitable for the present invention. A commercial source of CMC is TIC Pretested® Pre-hydrated® Tricalose® CMC 6000 powder, sold by TIC GUMS, Inc. Another preferred gelling agent is Klucel HXF hydroxypropyl cellulose. Another preferred embodiment is the combination of Action Gum 1144 and Klucel HXF as gelling agents, in the range of from 5 to 25 wt. % of the formulation.

In one embodiment of the present invention, the delivery system is a solid lipid suspension. The solid lipids of the present invention may be of animal, vegetable or mineral origin, which are substantially water-insoluble, inert, non-toxic hydrocarbon fats and oils and derivatives thereof, and may comprise any of the commonly commercially available fats or oils approved by the Food & Drug Administration, having melting points in the range of about 90 to 160° F. (32 to 71° C.). The lipid may comprise a vegetable oil base commonly known as hard butter, such as sold under the trademark KALOMEL™. Hard butters are hydrogenated, press fractionated, or other processed oils that are processed or recombined to have a solid fat index (percent solid fat vs. temperature) similar to that of cocoa butter. A preferred lipid is sold as Paramount C, a palm kernel oil with lecithin, that is partially hydrogenated. However, other lipids may be used that are relatively hard or solid at room temperature, but melt rapidly in the mouth at a temperature of about 92° to 98° F. (29 to 32° C.) (mouth temperature). The lipid is employed in the amounts within the range of from about 20 to 50%. When present below about 20%, the amount of lipid is not sufficient to completely coat the dry particles.

In a second embodiment of the present invention, the lipid is a liquid. Examples of suitable lipids include tallow, hydrogenated tallow, hydrogenated vegetable oil, almond oil, coconut oil, corn oil, cottonseed oil, light liquid petrolatum, heavy liquid petrolatum, olein, olive oil, palm oil, peanut oil, persic oil, sesame oil, soybean oil or safflower oil.

Additionally, stearines can be used in the present invention. The addition of stearines to the solid lipids provides the favorable property of mold-release. Further, the addition of stearines raises the melting point of the composition as high as about 100° F. (38° C.), which is particularly beneficial when the product is shipped or stored in unrefrigerated compartments.

The weight ratio of gelling agent to lipid is critical to the combination of tamper-resistance and drug-release properties of the dosage form. When the weight ratio of gelling agent to lipid is equal to or greater than about 1:1.4, the delivery system gels, but does not release the drug active into the digestive system. When the ratio is less than about 1:1.4, the drug active is released into the digestive system, but when the ratio of gelling agent to lipid is too low, the dosage form does not gel rapidly to retain the drug active. However, when the ratio is less than about 1:8, rapid gelling does not occur. A preferred range of gelling agent to lipid is from about 1:2 to 1:7. A more preferred range is from about 1:3 to 1:6.

The fillers of the present invention are pharmacologically inert and optionally nutritionally beneficial to humans and animals. Such fillers include cellulose such as microcrystalline cellulose, grain starches such as cornstarch, tapioca, dextrin, sugars and sugar alcohols such as sucrose, sorbitol, xylitol, and mannitol. The fillers may include one or more gelling agent. Preferred fillers include non-fat milk powder, whey, grain brans such as oat bran, and fruit and vegetable pulps. Preferred fillers are finely divided and have a preferred average particle size in the range of about 0.10 to 500 microns. The fillers are present in the drug delivery device in a concentration of about 50 to 80%. Optionally, the opioid particles can also serve as filler in the delivery system.

Optionally, an emulsifier or surfactant may be used in the lipid suspension. Any emulsifier or surfactant approved for use in foods by the Food and Drug Administration and having a relatively low HLB value, in the range of about 1 to 3, is suitable for use in the present invention. The appropriate surfactant minimizes the surface tension of the lipid, allowing it to oil wet and encapsulate the non-oil solid particles. Typically, the surfactant is present in the delivery system in the concentration of about 1.0 to 15.0 wt. %. Suitable surfactants include alkyl aryl sulfonate, alkyl sulfonates, sulfonated amides or amines, sulfated or sulfonated esters or ethers, alkyl sulfonates, of dioctyl sulfonosuccinate and the like, a hydrated aluminum silicate such as bentonite or kaolin, triglycerol monostearate, triglycerol monoshortening, monodiglyceride propylene glycol, octaglycerol monooleate, octaglycerol monostearate, and decaglycerol decaoleate. A preferred surfactant is lecithin, such as Solec 3F-SB, Durfax™ 80, an emulsifier made of sorbitan esters and ethoxylates, sold by Lodas Croklaan, TMaz 80K, an ethoxylated polysorbate monooleate, and Carbowax Sentry PEG3350, a polyethylene glycol. The preferred concentration of lecithin and/or Durfax™ 80 is from about 4.0 to 10.0 wt. %.

In a preferred embodiment, the acid salt of the sympathomimetic amine is microencapsulated. Such microencapsulation includes sustained release encapsulation. Any known method of encapsulation is suitable in the present invention. Such methods include, but are not limited to air coating, chemical erosion, coacervation, fluid bed coating, macroencapsulation, microencapsulation, osmosis, pan spray coating, physical erosion, polymer protein conjugate systems, and polymeric microspheres. A preferred method involves slowly blending the drug with a filming agent solution to form granulated particles. The granulated particles are allowed to dry on a tray and are sieved to the desired size, typically in the range of from about 200 to 500 microns. The coating materials include, but are not limited to, acrylic polymers and co-polymers, alginates, calcium stearate, cellulose, including methylcellulose, ethylcellulose, and hydroxypropyl cellulose, gelatins, glyceryl behenate, glycholic acid and its various forms, ion exchange resins, lactic acid and its various forms, lipids, methacrylic monomers, methacrylic polymers and co-polymers, polyethylene glycol polymers, shellac (pharmaceutical glaze), stearic acid, glycerol esters of fatty acids and waxes.

In a second embodiment, the acid salt of the sympathomimetic amine suspended in the lipid as dry particles, and the resulting dosage form is microencapsulated, so that not only the amine salt, but the lipid and other dry particles are microencapsulated. In a third embodiment, the lipid formulation is enclosed in a gel capsule, and the capsule is coated with a coating material for encapsulation.

In another embodiment of the present invention, the amine salt is not microencapsulated, but suspended in the lipid as dry particles. Typically the amine salt is present in the delivery device in a concentration of 30% or less. However, the amine salt can comprise all of the dried particles, to provide the necessary dose.

Optionally, the dry particles include flavorings that make the device taste and smell appealing to humans or animals. The flavorings can be natural or synthetic, and can include fruit flavorings, citrus, meat, chocolate, vanilla, fish, butter, milk, cream, egg or cheese. The flavorings are typically present in the device in the range of about 0.05 to 50.0%.

The delivery device may also include other pharmaceutically acceptable agents, such as additional analgesics, sweetening agents, including hydrogenated starch hydrolysates, synthetic sweeteners such as sorbitol, xylitol, saccharin salts, L-aspartyl-L-phenylalanine methyl ester, as well as coloring agents, other binding agents, lubricants, such as calcium stearate, stearic acid, magnesium stearate, antioxidants such as butylated hydroxy toluene, antiflatuants such as simethicone and the like. Additional agents include protease inhibitors, absorption enhancers and mucoadhesives.

Optionally, rupturing agents (also known as disintegrating agents) are used to rapidly deliver the sympathomimetic amine into the recipient's system. A typical disintegrating agent is a starch that swells in the presence of water. Various modified starches, such as sodium starch glycolate, currently marketed under the trade names EXPLOTAB® or VIVASTAR®, sold by JRS Pharma, are used as disintegrating agents. A preferred disintegrating agent is croscarmellose sodium, marketed as VIVASOL® also sold by JRS Pharma. Another preferred agent is silicified microcrystalline cellulose and is sold as Prosolv HD90. When ingested, the capsule or pellet with the disintegrating agent swells in the presence of gastric juices and ruptures.

In one embodiment of the present invention, the rupturing agent is present inside the microcapsule. As water penetrates the microcapsule, it swells the agent and ruptures the capsule, rapidly delivering the peptide to the system. Additional rupturing agents are disclosed in U.S. Pat. No. 5,567,439, which is hereby incorporated by reference.

In another embodiment, the rupturing agent is present in the lipid suspension, which ruptures the dosage, but leaves the microcapsules intact. This allows the delayed delivery of the drug farther along in the digestive system, in the intestines or the colon. The present invention is particularly effective in this embodiment, in that the ingested dosage may be chewable, where the dosage cleaves in the lipid suspension when chewed, but leaves the microcapsules intact. Tablets or gel capsules, when chewed, typically result in damage to or rupturing of the microcapsules defeating the effectiveness of the microcapsules.

In yet another embodiment, multiple drugs have multiple encapsulations, each containing a rupturing agent. The filming agents used for encapsulation are selected to disintegrate at selected pH conditions, which rupture and release each opioid agonist at desired locations in the digestive system. In another embodiment, the use of a mucoadhesive could effect the delivery of the acid salt of the sympathomimetic amine to the colon.

The process for preparing the above delivery system comprises melting the lipid and mixing with the surfactant. The dry particles are mixed with the melted lipid mixture to form a suspension which may exhibit pseudoplastic and/or thixotropic flow properties, and poured or molded to provide dosage forms.

The dry particles, which include the amine salt, filler and optional flavorings and additives, are pre-blended and typically have a particle size in the range of from about 50 to 450 microns. The pre-blended particles are gradually added to the heated lipid base until a high solid suspension is obtained, typically in the range of about 50 to 80 wt. % particles and from about 50 to 20 wt. % lipid. The preferred form of amine salt is the micronized form.

Slow addition of the dry particles is critical in the production of the device, to insure that the particles are suspended in their micronized state and not as agglomerated clumps. The mixing step is accomplished in a heated mixing device that insures thorough mixing of all materials with minimal shear, such as a planetary mixer or a scrape surface mixer. After the suspension is formed, the product is poured into molds and allowed to cool. De-molding and packaging are then performed. Alternatively, the suspension can be super-cooled and sheeted in a semi-soft format. The sheet is processed through forming rolls containing a design or configuration that embosses and forms the final shape.

Liquid lipid suspensions can be prepared by mixing the sympathomimetic amine, other dry particles and excipients with the liquid lipid. The suspension can be placed in gel capsules as dosage forms.

The following examples are to illustrate the claimed invention and are not intended to limit the claims in any way. All of the percentages are by weight unless otherwise indicated.

Control C-1

Solid Dosage Form with No Lipid

Control 1 was a dosage form formulated with red 40 Lake dye, instead of the sympathomimetic amine, which would allow a visual evaluation of the release properties of the formula. The dry ingredients, below were blended and placed in a gel capsule.

TABLE 1

| Ingredient | Weight % |
|---|---|
| Action Gum 1144 (gelling agent) | 20.0 |
| VIVASTAR ® (disintegrating agent) | 38.0 |
| VIVASOL ® (disintegrating agent) | 38.0 |
| Red 40 Lake (red dye) | 4.0 |

The gel capsule was placed in 500 mL of deionized water at 37° C. with stirring. After 10 minutes, only about 10% of the dye had released, demonstrating poor release properties.

Control C-2

A Solid Lipid Oral Dosage Form with a Gelling Agent

The Example can be prepared according to the following procedure.

Forming the Suspension

The lipid (Kaomel) was heated in a Hobart 5 Quart planetary mixer jacketed with a heating mantle in the range of about 140 to 150° F. (60 to 66° C.) and melted. The surfactant, lecithin, was added to the lipid with mixing, and the mixture was allowed to cool to about 135° F. (58° C.).

The dry particles, including Red 40 Lake (the drug active substitute), CMC 6000 (prehydrated cellulose gum, a gelling agent), Action Gum 1144 (guar gum and xanthan gum, a gelling agent), VIVASTAR (a disintegrating agent), VIVASOL (a disintegrating agent) and Durfax™ 80 (a surfactant), were screened to a particle size in the range of about 200 and 500 microns and dry-blended. The dry particles were slowly added incrementally to the lipid/surfactant mixture with mixing over a period of about 1 hour, and provided a smooth suspension with no lumps or agglomerations. It was cooled to about 70° F. (21° C.) and placed in a gel cap. See Table 2.

Forming a Lipid Suspension with a Gelling Agent: Lipid Ratio of 5:7

TABLE 2

| Ingredient | Weight % |
|---|---|
| Kaomel (lipid) | 35.0 |
| Lecithin (surfactant) | 1.0 |
| Red 40 Lake (the active substitute) | 2.0 |
| Action Gum 1144 (the gelling agent) | 12.5 |
| CMC 6000 (gelling agent) | 12.5 |
| VIVASTAR (disintegrating agent) | 15.0 |
| VIVASOL (disintegrating agent) | 15.0 |
| Durfax ™ 80 (surfactant) | 5.0 |

The formula of Control 2 was prepared with red 40 Lake as a drug active substitute. When the dose was crushed, the lipid suspension was deformed, but not crushed into a powder, since the suspension was malleable. The deformed lipid suspension could not be drawn into a syringe for injection. When mixed with water, a gel rapidly formed, which prevented water extraction of the drug active.

Control 2 was placed in a gel cap and added to 500 mL of water at 37° C. with stirring, but only partially released after 10 minutes. With gelling agent to lipid weight ratio of 25:35 (or 1:1.4), it appeared that the amount of gelling agent was too high.

Example 1

A Lipid Suspension with a Gelling Agent Lipid Ratio of 2:9

A lipid suspension was prepared according to the method given for Control 2. See Table 3.

TABLE 3

| Ingredient | Weight % |
|---|---|
| Kaomel (lipid) | 45.0 |
| Lecithin (surfactant) | 1.0 |
| Red 40 Lake (the active substitute) | 2.0 |
| Action Gum 1144 (the gelling agent) | 10.0 |
| CMC 6000 (gelling agent) | — |
| VIVASTAR (disintegrating agent) | 20.0 |
| VIVASOL (disintegrating agent) | 20.0 |
| Durfax ™ 80 (surfactant) | 3.00 |

The lipid suspension of Example 1 had favorable properties of malleability and tamper-resistance. When wet with 5 mL of water, it gelled and proved resistant to water extraction.

The lipid suspension of Example 1 was placed in a gel cap, and placed in 500 mL water at 37° C., where it readily dissolved, and released the red dye in about 10 minutes. The gelling agent:lipid weight ratio of 10:45 (1:4.5) with less gelling agent than Control 2, and was more conducive to release the drug active, while retaining tamper-resistant properties.

The following samples were prepared as disclosed above and tested for tamper resistance, as indicated by being difficult to extract with water or ethanol.

Extractability:

Water: Ten tablets were pulverized in a coffee grinder and the particles mixed with 150 mL of deionized water. The mixture was filtered with a coffee filter and evaluated as follows: "Poor" indicated that too much liquid (>20 mL) came through the filter. "OK" indicated that about 10 mL of liquid came through the filter. "Good" indicated that less liquid (<10 mL) came through the filter. "Very good" indicated that only a small amount (about 2.0 to 4.0 mL) came through the filter.

Ethanol: The same procedure was used as was for water, above. However, 118.35 g (150 mL) of ethanol/water 90/10 was used in place of 150 mL of water, to provide a volume equivalent.

Dissolution:

The dissolution test was run at 37° C., stirred at 50 rpm, in deionized water. If a tablet was dissolved in about 9 minutes or less, the results were "Excellent". If a table was at least 75% dissolved in 45 minutes, the results were "Good." If the tablet was still intact by greater than 25% after 45 minutes, the results were "Poor".

The results of the extractability and the dissolution tests are given in the Tables below.

TABLE 4

| | Run Number | | | | |
|---|---|---|---|---|---|
| Ingredient | C-3 | 2 | 3 | 4 | 5 |
| Paramount C (lipid) | 40.0 | 40.0 | 40.0 | 40.0 | 40.0 |
| Lecithin - Solec 3F-SB (surfactant) | 2.0 | 2.0 | 2.0 | 2.0 | 2.0 |

TABLE 4-continued

| Ingredient | C-3 | 2 | 3 | 4 | 5 |
|---|---|---|---|---|---|
| Powdered sugar placebo (drug active substitute) | 8.98 | 8.98 | 8.98 | 6.76 | 6.76 |
| Action Gum 1144 (the gelling agent) | 5.0 | 8.0 | 10.0 | 5.0 | 5.0 |
| Klucel HXF (gelling agent) | 5.0 | 8.0 | 10.0 | 8.0 | 8.0 |
| Prosolv HD90 (disintegrating agent) | 16.0 | 17.5 | 15.9 | 17.6 | 16.1 |
| VIVASOL (disintegrating agent) | 16.0 | 17.5 | 15.9 | 17.6 | 16.1 |
| TMaz 80K - Polysorbate (surfactant) | — | — | — | — | — |
| Carbowax Sentry PEG3350 (emulsifier) | — | — | — | — | — |
| Durfax ™ 80 (emulsifier) | 3.0 | 3.0 | 3.0 | 3.0 | 3.0 |
| Water Extraction* | Poor | Good | V. Good | Good | V. Good |
| Ethanol/water 90/10 Extraction* | Poor | OK | V. Good | OK | Good |
| Dissolution 50 rpm | | | | | |

*Poor, releases more than 20 mL; OK, releases about 10 mL; Good, releases 2-4 mL; V. Good, doesn't release.

TABLE 5

| Ingredient | C-4 | C-5 | 6 | 7 | 8 |
|---|---|---|---|---|---|
| Paramount C (lipid) | 40.0 | 40.0 | 40.0 | 40.0 | 40.0 |
| Lecithin - Solec 3F-SB (surfactant) | 2.0 | 2.0 | 2.0 | 2.0 | 2.0 |
| Powdered sugar placebo (drug active substitute) | 8.98 | 8.98 | 8.98 | 6.76 | 6.76 |
| Action Gum 1144 (the gelling agent) | 5.0 | 8.0 | 10.0 | 5.0 | 2.0 |
| Klucel HXF (gelling agent) | 5.0 | 8.0 | 10.0 | 8.0 | 8.0 |
| Prosolv HD90 (disintegrating agent) | 16.0 | 17.5 | 15.9 | 17.6 | 17.6 |
| VIVASOL (disintegrating agent) | 16.0 | 17.5 | 15.9 | 17.6 | 17.6 |
| TMaz 80K - Polysorbate (surfactant) | — | — | — | — | — |
| Carbowax Sentry PEG3350 (emulsifier) | — | — | — | — | — |
| Durfax ™ 80 (emulsifier) | 3.0 | 3.0 | 3.0 | 3.0 | 6.0 |
| Water Extraction | Poor | OK | V. Good | Good | Good |
| Ethanol/water 90/10 Extraction | Poor | OK | V. Good | OK | Poor |
| Dissolution 50 rpm | | Poor | Excellent | Excellent | Excellent |

TABLE 6

| Ingredient | 9 | 10 | C-6 | C-7 | C-8 |
|---|---|---|---|---|---|
| Paramount C (lipid) | 40.0 | 40.0 | 40.0 | 40.0 | 40.0 |
| Lecithin - Solec 3F-SB (surfactant) | 2.0 | 2.0 | 2.0 | 2.0 | 2.0 |
| Powdered sugar placebo (drug active substitute) | 6.76 | 6.76 | 6.76 | 6.76** | 4.76** |
| Action Gum 1144 (the gelling agent) | 0.5 | 0.5 | 2.0 | 0.75 | 0.75 |
| Klucel HXF (gelling agent) | 10.0 | 10.0 | 10.0 | 10.0 | 10.0 |
| Prosolv HD90 (disintegrating agent) | 17.4 | 17.4 | 16.6 | 18.7 | 18.7 |
| VIVASOL (disintegrating agent) | 17.4 | 17.4 | 16.6 | 18.7 | 18.7 |
| TMaz 80K - Polysorbate (surfactant) | — | — | — | — | — |
| Carbowax Sentry PEG3350 (emulsifier) | — | 6.0 | 6.0 | 3.0 | 3.0 |
| Durfax ™ 80 (emulsifier) | 6.0 | — | — | — | — |
| Water Extraction | Poor | — | Poor | Good | Poor |
| Ethanol/water 90/10 Extraction | Good | — | Poor | OK | Poor |
| Dissolution 50 rpm | | Good | Poor | Poor | |

**MALTRIN® placebo. MALTRIN® is the registered trademark for maltodextrins and corn syrup solids produced by Grain Processing Corporation (GPC).

TABLE 7

| Ingredient | C-9 | C-10 | C-11 | C-12 | C-13 |
|---|---|---|---|---|---|
| Paramount C (lipid) | 40.0 | 40.0 | 40.0 | 40.0 | 40.0 |
| Lecithin - Solec 3F-SB (surfactant) | 2.0 | 2.0 | 2.0 | 2.0 | 2.0 |
| Powdered sugar placebo (drug active substitute) | 4.51** | 6.76 | 6.76 | 6.76 | 6.76** |
| Action Gum 1144 (the gelling agent) | 1.0 | 1.0 | 10.0 | 6.0 | 5.0 |
| Klucel HXF (gelling agent) | 10.0 | 10.0 | 10.0 | 10.0 | 8.0 |
| Prosolv HD90 (disintegrating agent) | 18.7 | 19.7 | 14.4 | 15.0 | 15.6 |
| VIVASOL (disintegrating agent) | 18.7 | 19.7 | 14.4 | 15.0 | 15.6 |
| TMaz 80K - Polysorbate (surfactant) | — | — | — | — | — |
| Carbowax Sentry PEG3350 (emulsifier) | 3.0 | 1.0 | 0.5 | 1.0 | — |
| Durfax ™ 80 (emulsifier) | — | — | — | — | 6.0 |
| Water Extraction | Poor | Poor | Good | — | Good |
| Ethanol/water 90/10 Extraction | Poor | Poor | Poor | — | OK |
| Dissolution 50 rpm | Good | Good | Poor | Poor | Poor |

**MALTRIN placebo

TABLE 8

| Ingredient | 11 | 12 | 13 | 14 |
|---|---|---|---|---|
| Paramount C (lipid) | 40.0 | 40.0 | 41.0 | 41.1 |
| Lecithin - Solec 3F-SB (surfactant) | 2.0 | 2.0 | 2.0 | 2.0 |
| MALTRIN placebo (drug active substitute) | 6.76 | 11.27 | 6.03 | 6.70 |
| Action Gum 1144 (the gelling agent) | 0.5 | 0.5 | 0.6 | 0.7 |
| Klucel HXF (gelling agent) | 10.0 | 10.0 | 11.0 | 10.5 |
| Prosolv HD90 (disintegrating agent) | 17.4 | 15.2 | 16.0 | 16.0 |
| VIVASOL (disintegrating agent) | 17.4 | 15.2 | 16.0 | 16.0 |
| TMaz 80K - Polysorbate (surfactant) | — | — | 7.0 | 7.0 |
| Carbowax Sentry PEG3350 (emulsifier) | — | — | — | — |
| Durfax ™ 80 (emulsifier) | 6.0 | 6.0 | — | 6.0 |
| Water Extraction | OK | OK | OK | OK |
| Ethanol/water 90/10 Extraction | OK | OK | OK | Poor |
| Dissolution 50 rpm | | | Good | Good |

TABLE 9

| Ingredient | Run Number | | |
|---|---|---|---|
| | 15 | 16 | 17 |
| Paramount C (lipid) | 41.0 | 41.7 | 42.4 |
| Lecithin - Solec 3F-SB (surfactant) | 2.0 | 2.0 | 2.0 |
| MALTRIN placebo (drug active substitute) | 6.70 | 6.71 | 6.04*** |
| Action Gum 1144 (the gelling agent) | 1.0 | 10.0 | 10.0 |
| Klucel HXF (gelling agent) | 11.0 | 10.0 | 10.0 |
| Prosolv HD90 (disintegrating agent) | 15.0 | 12.8 | 12.8 |
| VIVASOL (disintegrating agent) | 15.0 | 12.8 | 12.8 |
| TMaz 80K - Polysorbate (surfactant) | 5.0 | — | 3.0 |
| Carbowax Sentry PEG3350 (emulsifier) | — | 1.0 | 1.0 |
| Durfax ™ 80 (emulsifier) | — | 3.0 | — |
| Water Extraction** | Good | Excellent | V. Good |
| Ethanol/water 90/10 Extraction** | OK | Good | V. Good |
| Dissolution 50 rpm | | | Good |

***Pseudoephedrine hydrochloride - not a placebo

Control samples C-3 through C-13 failed to provide either good extractability properties and/or good dissolution properties. All of the controls and samples in Table 4 have a gelling agent to lipid ratio less than 1:1.4. The concentrations and types of the surfactants, gelling agents, and disintegrating agents were varied.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description shall be interpreted as illustrative rather than limiting. Thus, the breadth and scope of the present invention should not be limited by any of the above-described exemplary embodiments, but should be defined only in accordance with the following claims appended hereto and their equivalents.

The invention claimed is:

1. A tamper-resistant drug delivery system comprising at least one lipid, at least one gelling agent and at least one sympathomimetic amine, wherein the gelling agent gels in the presence of water in about 10 seconds or less, and wherein the weight ratio of gelling agent to lipid is less than 1:1.4 and lipid is present in the delivery system from about 20 to 50 wt % of the system, and wherein the system is malleable or liquid at about room temperature, and at least one sympathomimetic amine releases into the digestive system when ingested.

2. The drug delivery system of claim 1, wherein the weight ratio of gelling agent to lipid is in the range of from 1:2 to 1:7.

3. The drug delivery system of claim 1, wherein the weight ratio of gelling agent to lipid is in the range of from 1:3 to 1:6.

4. The drug delivery system of claim 1, wherein the system contains at least one disintegrating agent.

5. The drug delivery system of claim 1, wherein the system contains at least one surfactant.

6. The drug delivery system of claim 1, wherein the drug active is pseudoephedrine.

7. A tamper-resistant drug delivery system comprising at least one lipid, at least one gelling agent and at least one sympathomimetic amine, wherein the gelling agent gels in the presence of water in about 10 seconds or less, and wherein the weight ratio of gelling agent to lipid is less than 1:1.4, wherein the system contains at least one disintegrating agent and at least one surfactant, and wherein the lipid is not a fatty acid, and the lipid is present in the delivery system from about 20 to 50 wt % of the system, and wherein at least one sympathomimetic amine releases into the digestive system when ingested.

8. The drug delivery system of claim 7, wherein the sympathomimetic amine is microencapsulated.

9. The drug delivery system of claim 7, wherein the lipid is a solid at room temperature.

10. The drug delivery system of claim 7, wherein the lipid is a liquid at room temperature.

11. The drug delivery system of claim 1, wherein the at least one gelling agent is selected from the group consisting of hyaluronic acid, a salt of hyaluronic acid, hydroxypropyl cellulose, carboxymethyl cellulose, guar gum, and a combination of guar gum and xanthan gum.

12. The drug delivery system of claim 7, wherein the at least one gelling agent is selected from the group consisting of hyaluronic acid, a salt of hyaluronic acid, hydroxypropyl cellulose, carboxymethyl cellulose, guar gum, and a combination of guar gum and xanthan gum.

13. The drug delivery system of claim 1, wherein the lipid is a solid at room temperature.

14. The drug delivery system of claim 1, wherein the sympathomimetic amine is a pharmaceutically acceptable salt of a sympathomimetic amine.

15. The drug delivery system of claim 7, wherein the sympathomimetic amine is a pharmaceutically acceptable salt of a sympathomimetic amine.

16. A solid tamper-resistant drug delivery system comprising at least one lipid, at least one gelling agent and a pharmaceutical acceptable salt of at least one sympathomimetic amine, wherein the gelling agent gels in the presence of water in about 10 seconds or less, and wherein the weight ratio of gelling agent to lipid is less than 1:1.4, wherein the system contains at least one disintegrating agent and at least one surfactant, and wherein the lipid is not a fatty acid, and the lipid is present in the delivery system from about 20 to 50 wt % of the system, and wherein at least one sympathomimetic amine releases into the digestive system when ingested.

17. The drug delivery system of claim 16, wherein the system gels in the presence of both water and water/ethanol solutions.

18. The drug delivery system of claim 16, wherein the at least one gelling agent is selected from the group consisting of hyaluronic acid, a salt of hyaluronic acid, hydroxypropyl cellulose, carboxymethyl cellulose, guar gum, and a combination of guar gum and xanthan gum.

19. The drug delivery system of claim 17, wherein the at least one gelling agent is selected from the group consisting of hyaluronic acid, a salt of hyaluronic acid, hydroxylpropyl cellulose, carboxymethyl cellulose, guar gum, and a combination of guar gum and xanthan gum.

20. The drug delivery system of claim 13, wherein the system is a sustained release dosage form.

* * * * *